United States Patent [19]

Herron

[11] Patent Number: 5,380,668
[45] Date of Patent: Jan. 10, 1995

[54] COMPOUNDS HAVING THE ANTIGENICITY OF HCG

[75] Inventor: James N. Herron, Salt Lake City, Utah

[73] Assignee: University of Utah Research Foundation, Salt Lake City, Utah

[21] Appl. No.: 89,994

[22] Filed: Jul. 6, 1993

[51] Int. Cl.⁶ .................. G01N 33/53; A61K 37/02; C07K 7/00; C07K 15/00
[52] U.S. Cl. .................................. 436/510; 436/814; 436/818; 530/327; 530/328; 530/329; 514/14; 514/15; 514/16; 514/17
[58] Field of Search ............... 514/14, 15, 16, 17; 530/327, 328, 329; 436/510, 814, 818

[56] References Cited

U.S. PATENT DOCUMENTS

| | | | |
|---|---|---|---|
| 4,071,314 | 1/1978 | Prugnaud | 23/230 B |
| 4,116,776 | 9/1978 | Dalbow et al. | 195/103.7 |
| 4,400,316 | 8/1983 | Katsuragi et al. | 260/112.5 R |
| 4,708,871 | 11/1987 | Geysen | 424/88 |
| 4,789,734 | 12/1988 | Pierschbacher | 530/395 |
| 4,804,626 | 2/1989 | Bellet et al. | 435/7 |
| 4,833,092 | 5/1989 | Geysen | 436/501 |
| 5,182,216 | 1/1993 | Clayton et al. | 436/518 |
| 5,194,392 | 3/1993 | Geysen | 436/518 |

FOREIGN PATENT DOCUMENTS 9009395  8/1990  WIPO ............................ C07K 1/04

OTHER PUBLICATIONS

Rott et al., J. Gen. Virol. vol. 72 pp. 1505–1514 1991.
Francis J. Morgan et al.; The Journal of Biological Chemistry; vol. 250, No. 13, Issue of Jul. 10, pp. 5247–5258, 1975.
Hormones (A–Plike); vol. 12; "Anterior-Pituitarylike Hormones"; pp. 557–563.

*Primary Examiner*—Robert J. Hill, Jr.
*Assistant Examiner*—Sheela J. Huff
*Attorney, Agent, or Firm*—Trask, Britt & Rossa

[57] ABSTRACT

Disclosed are compounds having antigenic binding affinity with antibodies directed against human chorionic gonadotropin. The compounds typically include or consist of an oligopeptide with the sequence:

$$AA1'\ AA2'\ AA3'\ AA4'\ AA5'\ AA6'$$

wherein AA1' is Gly, Asn, Ser, Phe, Arg Leu, or Lys; AA2' is Pro, Trp, Ala, Val, or Glu; AA3' is Arg, Gln, Ile, Met, Val, Thr, Ser, Gly, or Phe; AA4' is Tyr, Glu, Leu, Phe, Pro, or Thr; AA5' is Asp, Asn, Leu, Met, Val, Tyr, Ser, Ile, Ala, Gly, or Phe; and AA6' is Phe, Trp, Ala, Thr, Arg, Asp, or Val.

20 Claims, No Drawings

SEQUENCE LISTING ( 1 ) GENERAL INFORMATION:

( i i i ) NUMBER OF SEQUENCES:24

( 2 ) INFORMATION FOR SEQ ID NO:1:

( i ) SEQUENCE CHARACTERISTICS:
        ( A ) LENGTH:6 amino acids
        ( B ) TYPE:amino acid
        ( D ) TOPOLOGY:linear ( x i ) SEQUENCE DESCRIPTION:SEQ ID NO:1:

```
            Gly  Pro  Arg  Tyr  Asx  Phe
            1                   5
```

( 2 ) INFORMATION FOR SEQ ID NO:2:

( i ) SEQUENCE CHARACTERISTICS:
        ( A ) LENGTH:6 amino acids
        ( B ) TYPE:amino acid
        ( D ) TOPOLOGY:linear ( x i ) SEQUENCE DESCRIPTION:SEQ ID NO:2:
```
            Gly  Pro  Gln  Tyr  Leu  Trp
            1                   5
```

( 2 ) INFORMATION FOR SEQ ID NO:3:

( i ) SEQUENCE CHARACTERISTICS:
        ( A ) LENGTH:6 amino acids
        ( B ) TYPE:amino acid
        ( D ) TOPOLOGY:linear ( x i ) SEQUENCE DESCRIPTION:SEQ ID NO:3:
```
            Gly  Pro  Gln  Tyr  Met  Phe
            1                   5
```

( 2 ) INFORMATION FOR SEQ ID NO:4:

( i ) SEQUENCE CHARACTERISTICS:
        ( A ) LENGTH:6 amino acids
        ( B ) TYPE:amino acid
        ( D ) TOPOLOGY:linear ( x i ) SEQUENCE DESCRIPTION:SEQ ID NO:4:
```
            Gly  Pro  Gln  Tyr  Val  Phe
            1                   5
```

( 2 ) INFORMATION FOR SEQ ID NO:5:

( i ) SEQUENCE CHARACTERISTICS:
        ( A ) LENGTH:6 amino acids
        ( B ) TYPE:amino acid
        ( D ) TOPOLOGY:linear ( x i ) SEQUENCE DESCRIPTION:SEQ ID NO:5:
```
            Gly  Pro  Ile  Tyr  Asp  Phe
            1                   5
```

( 2 ) INFORMATION FOR SEQ ID NO:6:

( i ) SEQUENCE CHARACTERISTICS:
        ( A ) LENGTH:6 amino acids
        ( B ) TYPE:amino acid
        ( D ) TOPOLOGY:linear ( x i ) SEQUENCE DESCRIPTION:SEQ ID NO:6:
```
            Gly  Pro  Ile  Tyr  Tyr  Phe
            1                   5
```

( 2 ) INFORMATION FOR SEQ ID NO:7:

( i ) SEQUENCE CHARACTERISTICS:
        ( A ) LENGTH:6 amino acids
        ( B ) TYPE:amino acid
        ( D ) TOPOLOGY:linear ( x i ) SEQUENCE DESCRIPTION:SEQ ID NO:7:
```
            Gly  Pro  Ile  Tyr  Val  Phe
            1                   5
```

( 2 ) INFORMATION FOR SEQ ID NO:8:

( i ) SEQUENCE CHARACTERISTICS:
        ( A ) LENGTH:6 amino acids
        ( B ) TYPE:amino acid
        ( D ) TOPOLOGY:linear ( x i ) SEQUENCE DESCRIPTION:SEQ ID NO:8:
```
            Gly  Pro  Met  Tyr  Asp  Phe
            1                   5
```

( 2 ) INFORMATION FOR SEQ ID NO:9:

(i) SEQUENCE CHARACTERISTICS:
    (A) LENGTH:6 amino acids
    (B) TYPE:amino acid
    (D) TOPOLOGY:linear (xi) SEQUENCE DESCRIPTION:SEQ ID NO:9:
    Gly Pro Val Tyr Asn Phe
    1                5

(2) INFORMATION FOR SEQ ID NO:10:

(i) SEQUENCE CHARACTERISTICS:
        (A) LENGTH:6 amino acids
        (B) TYPE:amino acid
        (D) TOPOLOGY:linear (xi) SEQUENCE DESCRIPTION:SEQ ID NO:10:
        Gly Pro Val Tyr Ser Phe
        1                5

(2) INFORMATION FOR SEQ ID NO:11:

(i) SEQUENCE CHARACTERISTICS:
        (A) LENGTH:6 amino acids
        (B) TYPE:amino acid
        (D) TOPOLOGY:linear (xi) SEQUENCE DESCRIPTION:SEQ ID NO:11:
        Gly Pro Val Tyr Ile Phe
        1                5

(2) INFORMATION FOR SEQ ID NO:12:

(i) SEQUENCE CHARACTERISTICS:
        (A) LENGTH:6 amino acids
        (B) TYPE:amino acid
        (D) TOPOLOGY:linear (xi) SEQUENCE DESCRIPTION:SEQ ID NO:12:
        Asn Trp Arg Glu Ala Ala
        1                5

(2) INFORMATION FOR SEQ ID NO:13:

(i) SEQUENCE CHARACTERISTICS:
        (A) LENGTH:6 amino acids
        (B) TYPE:amino acid
        (D) TOPOLOGY:linear (xi) SEQUENCE DESCRIPTION:SEQ ID NO:13:
        Ser Ala Thr Leu Gly Thr
        1                5

(2) INFORMATION FOR SEQ ID NO:14:

(i) SEQUENCE CHARACTERISTICS:
        (A) LENGTH:6 amino acids
        (B) TYPE:amino acid
        (D) TOPOLOGY:linear (xi) SEQUENCE DESCRIPTION:SEQ ID NO:14:
        Phe Val Ser Phe Phe Arg
        1                5

(2) INFORMATION FOR SEQ ID NO:15:

(i) SEQUENCE CHARACTERISTICS:
        (A) LENGTH:6 amino acids
        (B) TYPE:amino acid
        (D) TOPOLOGY:linear (xi) SEQUENCE DESCRIPTION:SEQ ID NO:15:
        Lys Glu Phe Thr Phe Val
        1                5

(2) INFORMATION FOR SEQ ID NO:16:

(i) SEQUENCE CHARACTERISTICS:
        (A) LENGTH:7 amino acids
        (B) TYPE:amino acid
        (D) TOPOLOGY:linear ( x i ) SEQUENCE DESCRIPTION:SEQ ID NO:16:

Arg  Leu  Pro  Gly  Pro  Ser  Asp
    1               5

( 2 ) INFORMATION FOR SEQ ID NO:17:

( i ) SEQUENCE CHARACTERISTICS:
        ( A ) LENGTH:11 amino acids
        ( B ) TYPE:amino acid
        ( D ) TOPOLOGY:linear ( x i ) SEQUENCE DESCRIPTION:SEQ ID NO:17:

Gly  Gly  Arg  Leu  Pro  Gly  Pro  Ser  Asp  Cys  Gly
    1               5                        10

( 2 ) INFORMATION FOR SEQ ID NO:18:

( i ) SEQUENCE CHARACTERISTICS:
        ( A ) LENGTH:10 amino acids
        ( B ) TYPE:amino acid
        ( D ) TOPOLOGY:linear ( x i ) SEQUENCE DESCRIPTION:SEQ ID NO:18:

Gly  Arg  Leu  Pro  Gly  Pro  Ser  Asp  Cys  Gly
    1               5                        10

( 2 ) INFORMATION FOR SEQ ID NO:19:

( i ) SEQUENCE CHARACTERISTICS:
        ( A ) LENGTH:13 amino acids
        ( B ) TYPE:amino acid
        ( D ) TOPOLOGY:linear ( i x ) FEATURE:
        ( D ) OTHER INFORMATION:
            Xaa at position 13 is a-alanyl ( x i ) SEQUENCE DESCRIPTION:SEQ ID NO:19:

Gly  Ser  Gly  Ser  Ala  Gly  Pro  Ile  Tyr  Val  Phe  Gly  Xaa
    1               5                        10

( 2 ) INFORMATION FOR SEQ ID NO:20:

( i ) SEQUENCE CHARACTERISTICS:
        ( A ) LENGTH:13 amino acids
        ( B ) TYPE:amino acid
        ( D ) TOPOLOGY:linear ( i x ) FEATURE:
        ( D ) OTHER INFORMATION:
            Xaa at position 13 is a-alanyl ( x i ) SEQUENCE DESCRIPTION:SEQ ID NO:20:

Gly  Ser  Gly  Ser  Ala  Gly  Pro  Val  Tyr  Ser  Phe  Gly  Xaa
    1               5                        10

( 2 ) INFORMATION FOR SEQ ID NO:21:

( i ) SEQUENCE CHARACTERISTICS:
        ( A ) LENGTH:13 amino acids
        ( B ) TYPE:amino acid
        ( D ) TOPOLOGY:linear ( i x ) FEATURE:
        ( D ) OTHER INFORMATION:
            Xaa at position 13 is a-alanyl ( x i ) SEQUENCE DESCRIPTION:SEQ ID NO:21:

Gly  Ser  Gly  Ser  Ala  Gly  Pro  Arg  Tyr  Asn  Phe  Gly  Xaa
    1               5                        10

( 2 ) INFORMATION FOR SEQ ID NO:22:

( i ) SEQUENCE CHARACTERISTICS:
        ( A ) LENGTH:13 amino acids
        ( B ) TYPE:amino acid
        ( D ) TOPOLOGY:linear ( i x ) FEATURE:
        ( D ) OTHER INFORMATION:
            Xaa at position 13 is a-alanyl ( x i ) SEQUENCE DESCRIPTION:SEQ ID NO:22:

```
Gly Ser Gly Ser Ala Gly Pro Ile Tyr Asp Phe Gly Xaa
 1               5                   10
```

( 2 ) INFORMATION FOR SEQ ID NO:23:

( i ) SEQUENCE CHARACTERISTICS:
( A ) LENGTH:13 amino acids
( B ) TYPE:amino acid
( D ) TOPOLOGY:linear ( i x ) FEATURE:
( D ) OTHER INFORMATION:
Xaa at position 13 is a-alanyl ( x i ) SEQUENCE DESCRIPTION:SEQ ID NO:23:

```
Gly Ser Gly Ser Ala Gly Pro Gln Tyr Met Phe Gly Xaa
 1               5                   10
```

( 2 ) INFORMATION FOR SEQ ID NO:24:

( i ) SEQUENCE CHARACTERISTICS:
( A ) LENGTH:6 amino acids
( B ) TYPE:amino acid
( D ) TOPOLOGY:linear ( i x ) FEATURE:
( D ) OTHER INFORMATION:
Xaa at position 3 is substituted or
unsubstituted Arg, Gln, Ile, Met, Val,
Thr, Ser or Phe; Xaa at position 5 is substituted or
unsubstituted Asx, Leu, Met, Val, Tyr,
Ser, Ile, Ala, Gly or Phe ( x i ) SEQUENCE DESCRIPTION:SEQ ID NO:24:

```
Gly Pro Xaa Tyr Xaa Phe
 1               5
```

COMPOUNDS HAVING THE ANTIGENICITY OF HCG

TECHNICAL FIELD

The invention generally relates to peptides and related compounds, and more specifically to compounds containing a small peptide having the antigenicity of human chorionic gonadotropin.

BACKGROUND ART

Human chorionic gonadotropin (hCG) is a glycoprotein secreted by the placenta and excreted in the urine. Urinary levels of hCG are highest during the first trimester of pregnancy. Because of these facts, the detection of hCG in urine by way of diagnostic tests has been used in pregnancy determination kits and tests.

The glycoprotein itself has two sub-units, the sequence of which has been published. Morgan et al. "The Amino Acid Sequence of Human Chorionic Gonadotropin", *The Journal of Biological Chemistry*, 250(13):5247–5258 (1975).

Over the years, various investigators have worked on assays for hCG which would be both sensitive and specific and which would be useful as an early indication of pregnancy. In some cases, synthetic peptides of various lengths and amino acid sequences have been designed for potential use in binding to anti-hCG. For example, U.S. Pat. No. 4,400,316 to S. Katsuragi et al. relates to a peptide taken from the C-terminal fragment of hCG which comprises an amino acid sequence including fragment [127–145]. This patent refers to the synthesis of various protected hCG fragments in making the intended end-product including several containing six and seven amino acid residues: P(140–145); P(139–145); P(132–137); P(106–111); and P(105–111).

U.S. Pat. No. 4,804,626 to D. Bellet et al. describes an immunometric assay for the detection of hCG. It indicates that certain cell lines recognized antigenic determinants in certain residues of the C-terminus peptides: FB12 recognizing residues 110–116 and FB08 and FB09 recognizing residues 134–145, particularly the glycosylated 134–139. Bellet and co-workers synthesized certain subpeptides of lengths between five and ten amino acid residues: 110–116 and 139–145.

It would be an improvement in the art to have easily synthesizable short peptides having the antigenicity of a portion of the β-chain of hCG for use especially in diagnostic test kits.

DISCLOSURE OF THE INVENTION

It has been found that certain oligopeptides—including those not having the natural sequence of hCG—bind antigenically with antibodies directed against hCG. The invention thus includes these oligopeptides themselves, the use of these peptides, and methods of making them.

Compounds according to the invention contain an oligopeptide having the sequence:

AA1' AA2' AA3' AA4' AA5' AA6' wherein AA1' is Gly, Asn, Ser, Phe, Arg Leu, or Lys; AA2' is Pro, Trp, Ala, Val, or Glu; AA3' is Arg, Gln, Ile, Met, Val, Thr, Ser, Gly, or Phe; AA4' is Tyr, Glu, Leu, Phe, Pro, or Thr; AA5' is Asp, Asn, Leu, Met, Val, Tyr, Ser, Ile, Ala, Gly, or Phe; and AA6' is Phe, Trp, Ala, Thr, Arg, Asp, or Val.

The invention also includes the use of compounds which bind antigenically with an antibody directed against hCG in diagnostic tests and kits utilizing the compound's antigenic binding affinity for an antibody directed against hCG.

The invention further includes a process for preparing such compounds and oligopeptides, the process including coupling suitably protected amino acids or amino acid analogues, followed by removing the protecting groups.

BEST MODE OF THE INVENTION

Preferred compounds for use with invention contain a hexapeptide with the sequence:

AA1 AA2 AA3 AA4 AA5 AA6 wherein AA1 is Gly, Asn, Ser, Phe, or Lys; AA2 is Pro, Trp, Ala, Val, or Glu; AA3 is Arg, Gln, Ile, Met, Val, Thr, Ser, or Phe; AA4 is Tyr, Glu, Leu, Phe, or Thr; AA5 is Asp, Asn, Leu, Met, Val, Tyr, Ser, Ile, Ala, Gly, or Phe; and AA6 is Phe, Trp, Ala, Thr, Arg, or Val.

Especially preferred are such compounds wherein AA1 is Gly, AA2 is Pro, AA4 is Tyr, and/or AA6 is Phe.

"Compound", as used herein, refers to chemical compounds which contain or consist of the antigenic oligopeptide. For instance, the previously described preferred compound could be:

NT AA1 AA2 AA3 AA4 AA5 AA6 CT wherein NT at the N-terminus is selected from the group of small (e.g. 1 to 5 amino acids) peptides, H—, $CH_3$—, an acyl group, or a general protective group; and CT at the C-terminus is selected from the group of small (e.g. 1 to 5 amino acids) peptides, —OH, —OR$^1$, —NH$_2$, —NHR$^1$, —NR$^1$R$^2$, or —N(CH$_2$)$_{1-6}$NR$^1$R$^2$, wherein R$^1$ and R$^2$, when present, are independently selected from H, alkyl, aryl, (ar)alkyl, and wherein R$^1$ and R$^2$ can be cyclically bonded to one another.

"Alkyl" as used herein, is preferably a saturated branched or unbranched hydrocarbon having one to six carbon atoms, e.g. methyl, ethyl, and isopentyl.

"Aryl" as used herein, is an aromatic hydrocarbon group, preferably having 6 to 10 carbon atoms, such as phenyl or naphthyl.

"(Ar)alkyl", as used herein, is an arene group (having both aliphatic and aromatic portions), preferably having 7 to 13 carbon atoms such as benzyl, ethylbenzyl, n-propylbenzyl, and isobutylbenzyl.

"Oligopeptide", as used herein are peptides having from 6 to 13 amino acids joined together by peptide bonds. Equivalent to oligopeptides are compounds having the same or equivalent sidechains as the particular amino acids used in an oligopeptide, and arranged sequentially in the same order as the peptides, but joined together by non-peptide bonds, e.g. by isosteric linkages such as the keto isostere, hydroxy isostere, diketo isostere, or the keto-difluoromethylene isostere.

"Compound" also includes, for example, an acceptable salt of the oligopeptide or a labeled oligopeptide. As used herein, "acceptable salt" refers to salts that retain the desired activity (e.g. antigenicity) of the oligopeptide or equivalent compound, but preferably do not detrimentally affect the activity of the oligopeptide or other component of a system in which uses the oligopeptide. Examples of such salts are acid addition salts formed with inorganic acids, for example, hydrochloric acid, hydrobromic acid, sulfuric acid, phosphoric acid, nitric acid, and the like. Salts may also be formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, and the like. Salts may be formed with polyvalent metal cations such as zinc, calcium, bismuth, barium, magnesium, aluminum, copper, cobalt, nickel and the like or with an organic cation formed from N,N'-dibenzylethylenediamine or ethylenediamine, or combinations thereof (e.g. a zinc tannate salt).

A "substitution" with regard to the various amino acids (e.g. Phe) generally relate to substituting a group such as alkoxy, halogen, hydroxy, nitro, or lower alkyl onto an aromatic ring for a hydrogen that would usually be present. Substitutions can also be made on the alkyl chain connecting the aromatic portion to the peptide backbone, with, for instance lower alkyl groups substituting for a hydrogen. Still further substitutions can be made at the alpha position of an amino acid, also using an alkyl group.

Substitutions with regard to the amino acid phenylalanine include compounds such as L/D-homophenylalanyl, N methyl phenylalanyl, α-methylphenylalanyl, and α-methyl-tyrosyl.

Preferred substitutions involve the use of fluorine or chlorine as a halogen, and methoxy as an alkoxy group. With regard to alkyl and lower alkyl, generally alkyl groups having fewer (1 to 3) carbon atoms are preferred.

The compounds according to the general formula may be prepared in a manner conventional for such compounds. To that end, suitably $N^\alpha$ protected (and side-chain protected if reactive side-chains are present) amino acid derivatives or peptides are activated and coupled to suitably carboxyl protected amino acid or peptide derivatives either in solution or on a solid support. Protection of the α-amino functions generally takes place by urethane functions such as the acid-labile tertiary-butyloxycarbonyl group ("Boc"), benzyloxycarbonyl ("Z") group and substituted analogs or the base-labile 9-fluoremyl-methyloxycarbonyl ("Fmoc") group. The Z group can also be removed by catalytic hydrogenation, Other suitable protecting groups include the Nps, Bmv, Bpoc, Aloc, MSC, etc. A good overview of amino protecting groups is given in *The peptides, Analysis, Synthesis, Biology*, Vol. 3 E. Gross and J. Meienhofer, eds., (Academic Press, New York, 1981). Protection of carboxyl groups can take place by ester formation e.g. base-labile esters like methyl or ethyl, acid labile esters like tert. butyl or, substituted, benzyl esters or hydrogenolytically. Protection of side-chain functions like those of lysine and glutamic or aspartic acid can take place using the aforementioned groups. Protection of thiol, and although not always required, of guanidino, alcohol and imidazole groups can take place using a variety of reagents such as those described in *The Peptides, Analysis, Synthesis, Biology id.* or in *Pure and Applied Chemistry*, 59(3), 331–344 (1987). Activation of the carboxyl group of the suitably protected amino acids or peptides can take place by the azide, mixed anhydride, active ester, or carbodiimide method especially with the addition of catalytic and racemization-suppressing compounds like 1-N-N-hydroxybenzotriazole, N-hydroxysuccinimide, 3-hydroxy-4-oxo-3,4-dihydro-1,2,3,-benzotriazine, N-hydroxy-5norbornene-2,3-dicarboxyimide. Also the anhydrides of phosphorus based acids can be used. See, e.g. *The Peptides, Analysis, Synthesis, Biology, supra* and *Pure and Applied Chemistry*, 59(3), 331–344 (1987).

It is also possible to prepare the compounds by the solid phase method of Merrifield. Different solid supports and different strategies are known see, e.g. Barany and Merrifield in *The Peptides, Analysis, Synthesis, Biology*, Vol. 2, E. Gross and J. Meienhofer, eds., (Acad. Press, New York, 1980), Kneib-Cordonier and Mullen *Int. J. Peptide Protein Res.*, 30, 705–739 (1987) and Fields and Noble *Int. J. Peptide Protein Res.*, 35, 161–214 (1990). The synthesis of compounds in which a peptide bond is replaced by an isostere, can, in general, be performed using the previously described protecting groups and activation procedures. Procedures to synthesize the modified isosteres are described in the literature e.g. for the —$CH_2$—NH— isostere and for the —CO—$CH_2$— isostere.

Removal of the protecting groups, and, in the case of solid phase peptide synthesis, the cleavage from the solid support, can take place in different ways, depending on the nature of those protecting groups and the type of linker to the solid support. Usually deprotection takes place under acidic conditions and in the presence of scavengers. See, e.g. volumes 3, 5 and 9 of the series on *The Peptides Analysis, Synthesis, Biology*, supra.

Another possibility is the application of enzymes in synthesis of such compounds; for reviews see e.g. H. D. Jakubke in *The Peptides, Analysis, Synthesis, Biology*, Vol. 9, S. Udenfriend and J. Meienhofer, eds., (Acad. Press, New York, 1987).

Although possibly not desirable from an economic point of view, oligopeptides according to the invention could also be made according to recombinant DNA methods. Such methods involve the preparation of the desired oligopeptide thereof by means of expressing recombinant polynucleotide sequence which codes for one or more of the oligopeptides in question in a suitable microorganism as host. Generally the process involves introducing into a cloning vehicle (e.g. a plasmid, phage DNA, or other DNA sequence able to replicate in a host cell) a DNA sequence coding for the particular oligopeptide or oligopeptides, introducing the cloning vehicle into a suitable eucaryotic or procaryotic host cell, and culturing the host cell thus transformed. When a eucaryotic host cell is used, the compound may include a glycoprotein portion.

However made, the inventive compounds are useful, for among other things, in diagnostic tests utilizing the compounds' antigenic binding affinity for an antibody directed against hCG. In such instances, the compounds may be labeled or tagged with a labelling substance. Labelling substances typically used include various radioactive isotopes, fluorescent compounds, enzymes, dye sols, or metal compounds used as sol particles.

In one embodiment, compounds according to the invention are bound to, or incorporated into a suitable support for capturing antibody directed against hCG. Supports can include the inner wall of a microtest well or a cuvette, a tube or capillary, a membrane filter, test strip, or the surface of a particle such as a latex particle, bead, erythrocyte, dye sol, metal (e.g. gold) sol or metal containing compound as sol particle. After the antibody directed against hCG has bonded with the compound, a bodily fluid suspected of containing hCG (e.g. urine) can be passed by the thus bonded antibodies. If hCG is present, it will bond with the antibody. A second labeled antibody—or labeled compound in a competitive test—can then be used to determine whether or not hCG is present (i.e. bonded to the first antibody).

Other diagnostic test kits which can utilize the compound are known to those of skill in the art which may be adapted for use in the instant invention. For example, immunological diagnostic test kits include radioimmunoassay or enzyme immunoactivity assay ("EIA") as described in U.S. Pat. No. Re. 32,696 to Schuurs et al., the contents of which are incorporated by this reference. A light scattering immunoassay system are described in U.S. Pat. Nos. 4,979,821 and 5,017,009 assigned to Ortho Diagnostic Systems, Inc., the contents of which are incorporated by this reference. Diagnostic test kits using two monoclonal antibodies of high binding affinity are described in U.S. Pat. Nos. 4,376,110 and 4,486,530, assigned to Hybritech, Inc., the contents of both of which are incorporated by this reference.

The invention is further explained by reference to the following illustrative EXAMPLES.

EXAMPLES

If no configuration of the amino acid has been stated, the L form is intended.

A. The following abbreviations have been assigned to the solvents or reagents used:
DTT=dithiothriotol
DCM=dichloromethane
BSA=bovine serum albumin
HOAc=acetic acid
DMF=N,N-dimethylformamide
TFA=trifluoro-acetic acid
DIPCDI=diisopropylcarbodiimide
TMR=tetramethyl rhodamine B. The following abbreviations have been used for the various groups employed:
Ala=alanine
Arg=arginine
Asn=asparagine
Asp=aspartic acid
Cys=cysteine
Gln=glutamine
Glu=glutamic acid
Gly=glycine
His=histidine
Ile=isoleucine
Leu=leucine
Lys=lysine
Met=methionine
Phe=phenylalanine
Pro=proline
Ser=serine
Thr=threonine
Trp=tryptophan
Tyr=tyrosine
Val=valine C. All sequences mentioned herein are written according to the generally accepted convention wherein the N-terminal amino acid is on the left, and the C-terminal amino acid is on the right.

EXAMPLE I

The following compound was synthesized:
H$_2$N-Gly-Gly-Arg-Leu-Pro-Gly-Pro-Ser-Asp-Cys-Gly-COOH (SEQ ID NO:17)

Synthesis

This amino acid sequence was synthesized on an Applied Biosystem automated peptide synthesizer using Fmoc methodology. Stewart & Young (eds.), *Solid Phase Peptide Synthesis*, (Pierce, Rockford, Ill. 2nd ed. 1984). The crude peptide was purified on reversed phase HPLC to >98% purity. Amino acid analysis and fast atom bombardment (Fab) mass spectroscopy were used to confirm the chemical structure. The maleimide derivative of tetramethylrhodamine (mixture of 5- and 6-isomers) was purified using C-18 reversed phase FPLC (Pharmacia) to obtain pure isomers. The 5-isomer (the fraction of longer retention) was used to label the peptide. A mixture of 0.1 mM peptide and 0.15 mM dye was dissolved in 100 mM phosphate buffer (pH 6) and allowed to react for 24 hours at 4° C. After the incubation, the reaction mixture was separated on C-18 reversed phase FPLC. Good separation was achieved using a gradient of acetonitrile in water. The acetonitrile content was increased from 15% to 30% over a period of 20 minutes, followed by an isocratic elution at 30% acetonitrile. All solvents contained 0.1% trifluoroacetic acid. Fractions containing the labeled peptide were vacuum dried and analyzed by Fab mass spectroscopy. *Mass Spectrometry*; McCloskey, J. A. (ed.) (Academic Press, New York, 1990). The concentration of the peptide-TMR conjugate in solution was determined spectroscopically at 550 nm using an extinction coefficient $(\epsilon_{1cm}^{1M})$ of 60,000 cm-1M=1.

Binding with Anti-hCG

The binding of the synthesized peptide with an anti-hCG monoclonal antibody purified as per van Erp et al. *J. Immunol. Methods*, 140: 35–241 (1991) and directed against a portion of the β-subunit of hCG (provided by Organon-Teknika of Boxtel, NL) was determined by EIA. The peptide was conjugated through its thiol group to BSA using a heterobifunctional cross-linking reagent (succinimidyl 4-(N-maleimidomethyl)cyclohexane-1-carboxylate). The conjugates were first absorbed on the wells of a ninety-six well plate. Nonspecific binding sites on the surface was masked by unlabeled BSA. The anti-hCG antibody was allowed to react with both sample and control wells overnight at 4° C. Alkaline phosphatase labeled protein A was used for the color development. All samples showed positive results, indicating that the peptide binds with the antibody, while nine controls showed no response at all. Three other positive controls with hCG showed comparable responses to the peptide antigen.

EXAMPLE II

The peptide of EXAMPLE I was doubly labeled with fluorescein and TMR. Excess of fluorescein maleimide was first reacted with the peptide (containing two glycine spacers) at pH 6.5 for twenty-four hours. The reaction mixture was eluted at a flow rate of 1 ml/min with a linear AB gradient (B: 85%→70% in 25 min. and remains at 70% thereafter), where solvent A was 0.1% TFA in acetonitrile and B was 0.1% TFA in deionized water. The fluorescein labeled peptide (gly-gly-Pep-F) came off the C-18 column first, followed by the hydrolyzed fluorescein maleimide. The presence of peptide in the first fraction was confirmed by amine test using ninhydrin reagents. The gly-gly-Pep-F fraction was then reacted with TMR isothiocynate for overnight at a pH 8.5 and at room temperature. The reaction mixture was eluted on the C-18 column in a similar fashion. The second peak fraction was identified to be the fraction T-gly-gly-Pep-F by its UV-vis absorption spectra. Concentrations of the conjugates were determined from the absorbance at 556 nm using an extinction coefficient of 58,000 $M^{-1}cm^{-1}$ for TMR.

EXAMPLE III

The doubly labeled peptide of EXAMPLE II was used as a tracer antigen in a competitive fluorescence polarization immunoassay for hCG. The peptide-TMR conjugate bonded to the anti-hCG monoclonal antibody specifically with an antigen-binding affinity (Ka)

EXAMPLE V

An equilibrium constant for the peptide of EXAMPLE IV(a) was determined in a solution phase immunoassay with a second monoclonal antibody directed against hCG (also obtained from Organon-Teknika, bv of Boxtel, NL). The constant was 34.6 nM.

EXAMPLE VII

Spacer sequences Gly-Ser-Gly-Ser-Ala and Gly-βAla were added to the N-terminus and C-terminus respectively of the hexapeptides of EXAMPLE IV(a), EXAMPLE IV(d), EXAMPLE IV(f), EXAMPLE IV(h), and EXAMPLE IV(l). The compounds relative binding affinities with the second monoclonal antibody against hCG were determined by EIA, with the following results:

| Compound: | Krel |
| --- | --- |
| Gly—Ser—Gly—Ser—Ala—Gly—Pro—Ile—Tyr—Val—Phe—Gly—βAla | 6.6 (SEQ ID NO: 19) |
| Gly—Ser—Gly—Ser—Ala—Gly—Pro—Val—Tyr—Ser—Phe—Gly—βAla | 2.0 (SEQ ID NO: 20) |
| Gly—Ser—Gly—Ser—Ala—Gly—Pro—Arg—Tyr—Asn—Phe—Gly—βAla | 1.6 (SEQ ID NO: 21) |
| Gly—Ser—Gly—Ser—Ala—Gly—Pro—Ile—Tyr—Asp—Phe—Gly—βAla | 1.3 (SEQ ID NO: 22) |
| Gly—Ser—Gly—Ser—Ala—Gly—Pro—Gln—Tyr—Met—Phe—Gly—βAla | 1.0 (SEQ ID NO: 23) | of $1.5 \times 10^7$ at 6° C. Because of the large difference in polarization between bound and free tracers, hCG was able to be measured at a level between 600 and 4000 IU/ml (i.e. 1.3 to 8.7 nanomolar). This is a 100 fold improvement over systems published in the literature. This was even more unexpected since the thus synthesized compound was not glycosylated, whereas the naturally occurring sequence is at the Ser. Interference due to non-specific binding and blood serum fluorescence was negligible in this system.

EXAMPLE IV

The following hexapeptides were synthesized:
(a) Gly-Pro-Arg-Tyr-Asn-Phe (SEQ ID NO:1);
(b) Gly-Pro-Arg-Tyr-Asp-Phe (SEQ ID NO:1);
(c) Gly-Pro-Gln-Tyr-Leu-Trp (SEQ ID NO:2);
(d) Gly-Pro-Gln-Tyr-Met-Phe (SEQ ID NO:3);
(e) Gly-Pro-Gln-Tyr-Val-Phe (SEQ ID NO:4);
(f) Gly-Pro-Ile-Tyr-Asp-Phe (SEQ ID NO:5);
(g) Gly-Pro-Ile-Tyr-Tyr-Phe (SEQ ID NO:6);
(h) Gly-Pro-Ile-Tyr-Val-Phe (SEQ ID NO:7);
(i) Gly-Pro-Met-Tyr-Asp-Phe (SEQ ID NO:8);
(j) Gly-Pro-Val-Tyr-Asn-Phe (SEQ ID NO:9);
(k) Gly-Pro-Val-Tyr-Ile-Phe (SEQ ID NO:11); and
(l) Gly-Pro-Val-Tyr-Ser-Phe (SEQ ID NO:10).

EXAMPLE VIII

EXAMPLE VII was repeated using TMR attached to the N-terminal amino group of each peptide, giving very similar results.

EXAMPLE IX

The following hexapeptides were synthesized:
(a) Asn-Trp-Arg-Glu-Ala-Ala (SEQ ID NO:12);
(b) Ser-Ala-Thr-Leu-Gly-Thr (SEQ ID NO:13);
(c) Phe-Val-Ser-Phe-Phe-Arg (SEQ ID NO:14); and
(d) Lys-Glu-Phe-Thr-Phe-Val (SEQ ID NO:15).

EXAMPLE X

The hexapeptides of EXAMPLE VIII were tested in both solution phase and solid phase immunoassays using a third monoclonal antibody directed against hCG (and also obtained from Organon-Teknika, bv of Boxtel, NL). In solid phase immunoassays, each peptide bonded with the monoclonal antibody. However, none of these hexapeptides bonded with the monoclonal antibody in solution phase immunoassays, implying that the binding constant probably had a relatively low affinity ($Kd \geq 10^{-5}M$).

Although the invention has been described with the use of various examples and preferred embodiments, these are illustrative only, and the scope of the invention is to be determined by the appended claims.

What is claimed is:

1. A compound which has up to 13 amino acids and which includes a hexapeptide with the sequence:

AA1 AA2 AA3 AA4 AA5 AA6 wherein:
AA1 is a substituted or unsubstituted amino acid, said amino acid selected from the group consisting of Gly, Asn, Ser, Phe, and Lys;
AA2 is a substituted or unsubstituted amino acid, said amino acid selected from the group consisting of Pro, Trp, Ala, Val, and Glu;
AA3 is a substituted or unsubstituted amino acid, said amino acid selected from the group consisting of Arg, Gln, Ile, Met, Val, Thr, Ser, and Phe;
AA4 is a substituted or unsubstituted amino acid, said amino acid selected from the group consisting of Tyr, Glu, Phe, and Thr;
AA5 is a substituted or unsubstituted amino acid, said amino acid selected from the group consisting of Asp, Asn, Leu, Met, Val, Tyr, Ser, Ile, Ala, Gly, and Phe; and
AA6 is a substituted or unsubstituted amino acid, said amino acid selected from the group consisting of Phe, Trp, Ala, Thr, Arg, and Val.

2. The compound of claim 1 wherein AA1 is Gly.
3. The compound of claim 1 wherein AA2 is Pro.
4. The compound of claim 1 wherein AA4 is Tyr.
5. The compound of claim 1 wherein AA6 is Phe.
6. The compound of claim 1 wherein the hexapeptide has the sequence of Gly-Pro-Ile-Tyr-Val-Phe (SEQ ID NO:7).

7. The compound of claim 1 wherein the hexapeptide has the sequence of Gly-Pro-Val-Tyr-Ser-Phe (SEQ ID NO:10).
8. The compound of claim 1 wherein the hexapeptide has the sequence of Gly-Pro-Arg-Tyr-Asn-Phe or Gly-Pro-Arg-Tyr-Asp-Phe (SEQ ID NO:1).
9. The compound of claim 1 wherein the hexapeptide has the sequence of Gly-Pro-Ile-Tyr-Asp-Phe (SEQ ID NO:5).
10. The compound of claim 1 wherein the hexapeptide has the sequence of Gly-Pro-Gln-Tyr-Met-Phe (SEQ ID NO:3).
11. The compound of claim 1 wherein the hexapeptide has the sequence of Asn-Trp-Arg-Glu-Ala-Ala (SEQ ID NO:12).
12. The compound of claim 1 wherein the hexapeptide has the sequence of Phe-Val-Ser-Phe-Phe-Arg (SEQ ID NO:14).
13. The compound of claim 1 wherein the hexapeptide has the sequence of Lys-Glu-Phe-Thr-Phe-Val (SEQ ID NO:15).
14. The compound of claim 1 wherein said compound is an oligopeptide.
15. The compound of claim 1 wherein said compound includes a labelling substance.
16. An oligopeptide having a binding affinity for an antibody directed against hCG, said oligopeptide selected from the group of oligopeptides consisting of:
Gly-Pro-Arg-Tyr-Asn-Phe (SEQ ID NO:1);
Gly-Pro-Arg-Tyr-Asp-Phe (SEQ ID NO:1);
Asn-Trp-Arg-Glu-Ala-Ala (SEQ ID NO:12);
Gly-Pro-Gln-Tyr-Leu-Trp (SEQ ID NO:2);
Gly-Pro-Gln-Tyr-Met-Phe (SEQ ID NO:3);
Gly-Pro-Gln-Tyr-Val-Phe (SEQ ID NO:4);
Gly-Pro-Ile-Tyr-Asp-Phe (SEQ ID NO:5);

Gly-Pro-Ile-Tyr-Tyr-Phe (SEQ ID NO:6);
Gly-Pro-Ile-Tyr-Val-Phe (SEQ ID NO:7);
Gly-Pro-Met-Tyr-Asp-Phe (SEQ ID NO:8);
Gly-Pro-Val-Tyr-Asn-Phe (SEQ ID NO:9);
Gly-Pro-Val-Tyr-Ile-Phe (SEQ ID NO:11);
Gly-Pro-Val-Tyr-Ser-Phe (SEQ ID NO:10);
Arg-Leu-Pro-Gly-Pro-Ser-Asp (SEQ ID NO:16);
Ser-Ala-Thr-Leu-Gly-Thr (SEQ ID NO:13);
Phe-Val-Ser-Phe-Phe-Arg (SED ID NO:14); and
Lys-Glu-Phe-Thr-Phe-Val (SEQ ID NO:15).

17. The oligopeptide of claim 16 wherein said oligopeptide has the sequence of Ser-Ala-Thr-Leu-Gly-Thr (SEQ ID NO:13).

18. The oligopeptide of claim 16 wherein said oligopeptide is Arg-Leu-Pro-Gly-Pro-Ser-Asp (SEQ ID NO:16).

19. A method of using an oligopeptide comprising the sequence:

AA1' AA2' AA3' AA4' AA5' AA6' wherein

AA1' is either Arg-Leu or a substituted or unsubstituted amino acid, said amino acid selected from the group consisting of Gly, Asn, Ser, Phe, and Lys;

AA2' is a substituted or unsubstituted amino acid, said amino acid selected from the group consisting of Pro, Trp, Ala, Val, and Glu;

AA3' is a substituted or unsubstituted amino acid, said amino acid selected from the group consisting of Arg, Gln, Ile, Met, Val, Thr, Ser, Gly, and Phe;

AA4' is a substituted or unsubstituted amino acid, said amino acid selected from the group consisting of Tyr, Glu, Leu, Phe, Pro, and Thr;

AA5' is a substituted or unsubstituted amino acid, said amino acid selected from the group consisting of Asx, Leu, Met, Val, Tyr, Ser, Ile, Ala, Gly, and Phe; and AA6' is a substituted or unsubstituted amino acid, said amino acid selected from the group consisting of Phe, Trp, Ala, Thr, Arg, Asp, and Val:

in a diagnostic test, said method comprising reacting the oligopeptide with an antibody directed against hCG.

20. The method of claim 19 wherein said oligopeptide is nonglycosylated.

* * * * *

UNITED STATES PATENT AND TRADEMARK OFFICE
CERTIFICATE OF CORRECTION

PATENT NO. : 5,380,668
DATED : January 10, 1995
INVENTOR(S) : James N. Herron

It is certified that error appears in the above-indentified patent and that said Letters Patent is hereby corrected as shown below:

In Column 2, line 45, insert a comma after "Aryl";

In Column 3, line 47, change the comma to a period;

In Column 3, line 50, capitalize "peptides";

In Column 6, line 34, at the end of the equation change "=1" to -- -1 --;

In Column 6, line 39, change "35" to --235--;

In Column 13, SEQ ID 19 (D), change "a-alanyl" to --β-alanyl--;

In Column 13, SEQ ID 20 (D), change "a-alanyl" to --β-alanyl--;

In Column 13, SEQ ID 21 (D), change "a-alanyl" to --β-alanyl--;

In Column 13, SEQ ID 22 (D), change "a-alanyl" to --β-alanyl--;

In Column 15, SEQ ID 23 (D), change "a-alanyl" to --β-alanyl--;

In Column 15, line 67, change "Ile" to --Ile--; and

In Column 18, line 19, change the colon to a semicolon.

Signed and Sealed this

Eighteenth Day of April, 1995

Attest:

BRUCE LEHMAN

Attesting Officer

Commissioner of Patents and Trademarks